United States Patent [19]
Hunter et al.

[11] 3,968,138
[45] July 6, 1976

[54] 6-CYANO-2,4-DINITRO-1,3-PHENYLENEDIAMINES

[75] Inventors: Don L. Hunter, Anaheim; William G. Woods, Fullerton; James D. Stone, Whittier, all of Calif.; Cecil W. LeFevre, Franklin, Idaho

[73] Assignee: United States Borax & Chemical Corporation, Los Angeles, Calif.

[22] Filed: Feb. 10, 1975

[21] Appl. No.: 549,243

Related U.S. Application Data

[62] Division of Ser. No. 86,386, Nov. 2, 1970, Pat. No. 3,910,783.

[52] U.S. Cl. .............................. 260/465 E; 71/105; 71/121; 260/465 G; 260/577
[51] Int. Cl.² .................................. C07C 121/78

[58] Field of Search .................... 260/465 E, 577

[56] References Cited
UNITED STATES PATENTS

| | | | |
|---|---|---|---|
| 3,257,190 | 6/1966 | Soper | 260/465 X |
| 3,617,251 | 2/1972 | Hunter et al. | 260/577 X |
| 3,654,363 | 4/1972 | Pum et al. | 260/577 |

*Primary Examiner*—Joseph Paul Brust
*Assistant Examiner*—Dolph H. Torrence
*Attorney, Agent, or Firm*—James R. Thornton

[57] ABSTRACT

2,4-Dinitro-1,3-phenylenediamine compounds having a lower alkyl or cyano substituent at the 6-position of the ring are useful as herbicides.

6 Claims, No Drawings

6-CYANO-2,4-DINITRO-1,3-PHENYLENEDIAMINES

This is a division of application Ser. No. 86,386, filed Nov. 2, 1970, now U.S. Pat. No. 7,910,783.

This invention relates to 2,4-dinitro-1,3-phenylenediamine compounds and their use as herbicides. There is provided by this invention a class of 2,4-dinitro-N-substituted-1,3-phenylenediamine compounds having an alkyl or cyano substituent in the 6-position of the aromatic ring. The compounds have outstanding herbicidal activity.

The herbicidal compounds of this invention can be defined by the formula

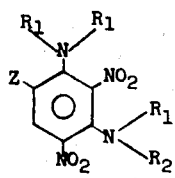

wherein Z is lower alkyl or cyano, each $R_1$ is selected from hydrogen, alkyl and alkenyl and $R_2$ is selected from alkyl and alkenyl.

For convenience in naming the compounds, the amino nitrogen adjacent to the alkyl or cyano group is referred to as $N^1$ and the amino nitrogen between the nitro groups on the ring is referred to as $N^3$. Thus, the nitro substituents are in the 2 and 4 position of the aromatic ring and the alkyl or cyano group is in the 6 position of the aromatic ring. It will be noted from the above definition that the $N^3$ amino nitrogen must have at least one hydrocarbon substituent thereon, thereby excluding the compounds having an unsubstituted amino ($-NH_2$) group at this position.

Typical examples of hydrocarbon groups represented by $R_1$ and $R_2$ as defined above are the lower alkyl and lower alkenyl groups having up to about 6 carbon atoms, including the cyclic analogues thereof as well as the halo and lower alkoxy substituted derivatives thereof. Representative groups are methyl, ethyl, n-propyl, isopropyl, n-butyl, sec-butyl, n-pentyl, sec-pentyl, n-hexyl, allyl, 2-butenyl, methallyl, 2-methoxyethyl, 3-ethoxypropyl, 2-chloroallyl, 2-bromoallyl, 2-bromoethyl, 1-methyl-2-methoxyethyl, 4-chloro-2-butenyl, 4-bromo-1-butenyl, 3-iodo-2-pentenyl, cyclohexyl, cyclopropyl, cyclobutyl, cyclohexenyl, and the like.

As set forth above, Z can represent a cyano ($-CN$) group or a lower alkyl group, preferably having 1 to 4 carbon atoms, such as methyl, ethyl, n-propyl, n-butyl, isopropyl, sec-butyl, and the like.

Representative examples of compounds of this invention are:

$N^1$-ethyl-$N^3$,$N^3$-diallyl-2,4-dinitro-6-methyl-1,3-phenylenediamine $N^1$-methyl-$N^3$-sec-butyl-2,4-dinitro-6-cyano-1,3-phenylenediamine $N^1$-ethyl-$N^3$-sec-butyl-2,4-dinitro-6-methyl-1,3-phenylenediamine $N^1$-methyl-$N^3$,$N^3$-di-n-propyl-2,4-dinitro-6-isopropyl 1,3-phenylenediamine $N^3$,$N^3$-di-n-propyl-2,4-dinitro-6-methyl-1,3-phenylenediamine $N^1$-methyl-$N^3$,$N^3$-diethyl-2,4-dinitro-6-cyano-1,3-phenylenediamine $N^3$,$N^3$-diethyl-2,4-dinitro-6-ethyl-1,3-phenylenediamine $N^3$-(3-pentyl)-2,4-dinitro-6-cyano-1,3-phenylenediamine $N^1$-methyl-$N^3$-(1-methyl-2-methoxyethyl)-2,4-dinitro-6-methyl-1,3-phenylenediamine $N^1$-methyl-$N^3$-cyclopropyl-2,4-dinitro-6-ethyl-1,3-phenylenediamine $N^1$-sec-pentyl-$N^3$,$N^3$-dimethyl-2,4-dinitro-6-methyl 1,3-phenylenediamine $N^3$-(3-chloro-n-propyl)-2,4-dinitro-6-methyl-1,3-phenylenediamine $N^3$-(4-heptyl)-2,4-dinitro-6-methyl-1,3-phenylenediamine $N^3$-(4-chloro-2-butenyl)-2,4-dinitro-6-methyl-1,3-phenylenediamine $N^3$-sec-butyl-2,4-dinitro-6-methyl-1,3-phenylenediamine The compounds of this invention are either crystalline solids or high boiling liquids. Generally they are only slightly soluble in water and are moderately soluble in the usual organic solvents such as ethanol, acetone, ether and benzene. The compounds are readily prepared by reaction of one or two amines or ammonia with a 2,4-dihalo-3,5-dinitroalkylbenzene or -benzonitrile according to the following equation:

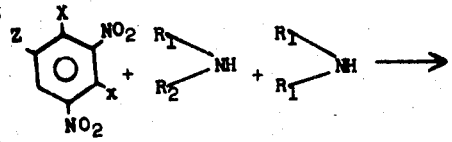

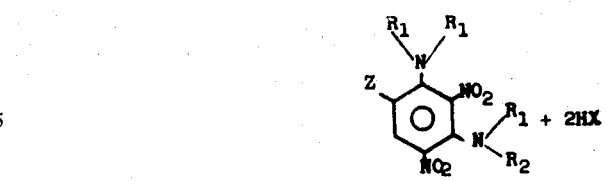

in which X is a reactive halogen such as bromo or chloro and Z, $R_1$ and $R_2$ have the significance previously assigned. When

and

are the same, that is when the substituted $N^1$ amino group is the same as the substituted $N^3$ amino group in the resultant product, the reaction can take place in one step using at least two moles of the amine for each mole of 2,4-dihalo-3,5-dinitrobenzene compound. The hydrogen halide can be neutralized by excess amine or a tertiary amine. When

is different from

the reaction requires two steps in which a different amine (or ammonia) is employed in each step. In the first step about two moles of the amine forming the $N^3$ group is reacted with about one mole of the 2,4-dihalo- 3,5-dinitrobenzene compound. The first halogen atom replaced is that between the nitro groups on the aromatic ring. This step can be carried out in a sealed reaction vessel or at atmospheric pressure in a solvent such as a hydrocarbon in which the amine hydrohalide is insoluble and can be removed by filtration. In the second step about two moles of the amine forming the $N^1$ group is reacted with the monoamino-substituted compound to form the unsymmetrically substituted 1,3-phenylenediamine compound. The second reaction is advantageously carried out in a sealed reaction vessel, such as a sealed tube or an autoclave, or at atmospheric pressure in the presence of a solvent, such as an alcohol or high boiling ether in which the amine is highly soluble. In the case of higher boiling amines it is not necessary to use a sealed reaction vessel for the reaction but it is sufficient merely to carry it out in the presence of a suitable solvent.

A reaction temperature in the range of from about 20° to about 120°C. preferably is employed to give good yields of the desired product and a satisfactory rate of reaction, both in the case of using a sealed reaction vessel and when the reactants are brought together at atmospheric pressure. Hydrogen halide is formed as a by-product and, in the presence of excess amine, is converted to the amine hydrohalide which can be readily removed by washing with water or by filtration after dissolution of the product in a suitable solvent. The desired products can be purified by well known procedures such as by recrystallization.

The following examples describe preparation of representative compounds of this invention but it is to be understood that the invention is not to be limited to the specific examples given.

EXAMPLE I

N-(3-pentyl)-3-chloro-2,6-dinitro-4-methylaniline

3-Pentylamine (10.4 g.; 0.1194 mole) and 2,4-dichloro-3,5-dinitrotoluene (15.0 g.; 0.0597 mole) in 30 ml. of dimethoxyethane were charged to a 50 ml. reaction tube. The tube was sealed and placed in an oven at 94°C. for 22 hours. The tube was then opened and the contents were evaporated to dryness under reduced pressure to leave an orange residue. The residue was extracted with 200 ml. of boiling hexane for one hour. After cooling the mixture was filtered and the filter cake washed with hexane. The filtrate was evaporated to an orange oil which slowly crystallized. The residual oil was taken up in 60 ml. of refluxing 95% EtOH and on cooling the product crystallized. The product was isolated by filtration and dried to give 9.18 g. of N-(3-pentyl)-3-chloro-2,6-dinitro-4-methylaniline, m.p. 61°-62.5°C. After recrystallization from 95% EtOH, the product melts at 62°-63.5°C.

$N^3$-(3-pentyl)-2,4-dinitro-6-methyl-1,3-phenylenediamine

A mixture of 5.00 g. (0.0165 mole) of N-(3-pentyl)-3-chloro-2,6-dinitro-4-methylaniline and 30 ml. of dimethoxyethane was charged to a glass reaction tube. The tube was cooled, 5 ml. of anhydrous ammonia condensed into it, and the tube was then sealed. After heating for 5 hours at 94°C., the tube was opened and the reaction mixture was stripped of volatile material. The residue was taken up in 250 ml. of hot cyclohexane, the solution filtered while hot, then stripped to give an orange residue which was crystallized from 95% ethanol to give 1.02 g. of the desired product as orange needles, m.p. 157°-160.5°C. After recrystallization from 95% ethanol the product melts at 160°-161.5°C.

EXAMPLE II $N^3,N^3$-diethyl-2,4-dinitro-6-methyl-1,3-phenylenediamine

This compound was prepared in a similar manner by reaction of N,N-diethyl-3-chloro-2,6-dinitro-4-methylaniline with ammonia. The crystalline product melts at 108°-109°C.

EXAMPLE III $N^3,N^3$-di-n-propyl-2,4-dinitro-6-methyl-1,3-phenylenediamine

This compound was prepared in a similar manner by reaction of N,N-di-n-propyl-3-chloro-2,6-dinitro-4-methylaniline with ammonia. The crystalline product melts at 126°-127°C.

EXAMPLE IV $N^3$-sec-butyl-2,4-dinitro-6-methyl-1,3-phenylenediamine

This compound was prepared in a similar manner by reaction of N-sec-butyl-3-chloro-2,6-dinitro-4-methylaniline with ammonia. The crystalline product melts at 151.5°-152.5°C.

EXAMPLE V $N^3$-(3-pentyl)-2,4-dinitro-6-ethyl-1,3-phenylenediamine 2,4-Dichloroethylbenzene (prepared by Wolff-Kishner reduction of 2,4-dichloroacetophenone) was nitrated by reaction with a mixture of nitric and sulfuric acids. The resultant 2,4-dichloro-3,5-dinitroethylbenzene was aminated with 3-pentylamine and then ammonia according to the procedure of Example I to give $N^3$-(3-pentyl)-2,4-dinitro-6-ethyl-1,3-phenylenediamine, m.p. 156.5°-157.5°C.

EXAMPLE VI

N,N-diethyl-3-chloro-2,6-dinitro-4-cyanoaniline

To a mixture of 4.65 g. (0.0177 mole) of 2,4-dichloro-3,5-dinitrobenzonitrile and 200 ml. of dimethoxyethane was added 2.59 g. (0.0354 mole) of diethylamine in 20 ml. of dimethoxyethane. The amine was added dropwise to the stirred solution at room temperature over a period of 3 hours. The reaction mixture was then stirred an additional 17 hours at room temperature. The reaction mixture was evaporated to dryness and the residue extracted with 200 ml. of diethyl ether. The ether solution was filtered and then evaporated to dryness to give 4.33 g. (82%) of N,N-diethyl-3-chloro-2,6-dinitro-4-cyanoaniline, identified by its nuclear magnetic resonance spectrum.

$N^3,N^3$-diethyl-2,4-dinitro-6-cyano-1,3-phenylenediamine

A solution of 4.33 g. (0.0144 mole) of N,N-diethyl-3-chloro-2,6-dinitro-4-cyanoaniline, 6.40 g. (0.0288 mole) of a 7.66% solution of ammonia in absolute ethanol, and 15 ml. of dimethoxyethane was sealed in a Pyrex reaction tube and alloed to stand at room temperature for 72 hours. The contents were distilled to dryness at reduced pressure and extracted with 100 ml. of boiling chloroform. The filtered chloroform extract was evaporated to dryness and the residual orange solid taken up in hot 95% ethanol. Upon cooling, the product crystallized and was isolated by filtration to give 1.51 g. (37.3%) or an orange, crystalline solid melting at 142°–145°C. Recrystallization from 95% ethanol gave the desired product, m.p. 145.5°–146.5°C.

EXAMPLE VII $N^1,N^3$-diethyl-2,4-dinitro-6-methyl-1,3-phenylenediamine

A glass reaction tube was charged with a solution of 5.0 g. (0.02 mole) of 2,4-dichloro-3,5-dinitrotoluene in 15 ml. of 1,2-dimethoxyethane. The tube was then chilled in a Dry Ice-acetone bath and 5.64 g. of 70% aqueous ethylamine (0.0876 mole) was added. The tube was then sealed, warmed gently and shaken to provide a homogeneous solution and then heated in an oven at 110°C. for 20 hours. The reaction mixture was removed from the tube and the solvent and volatiles removed by distillation under reduced pressure. Absolute ethanol was added to the solid residue and then stripped to remove the last traces of water. The dried residue was extracted with 200 ml. of refluxing diethyl ether for one hour and the cooled mixture filtered to removed insoluble amine hydrohalide. The ether filrate was evaporated to dryness to give a solid orange crystalline product. Recrystallization from 95% ethanol gave 3.96 g. (74%) of product melting at 59.5°–61.5°C.

EXAMPLE VIII $N^1$, $N^3$-diisopropyl-2,4-dinitro-6-methyl-1,3-phenylenediamine This compound was prepared in a similar manner by reaction of 2,4-dichloro-3,5-dinitrotoluene with isopropylamine to give the crystalline product melting at 96°–97°C.

The 3,5-dinitro-2,4-dihalo-alkylbenzene and -benzonitrile starting materials are prepared by known nitration reactions of the corresponding 2,4-dihaloalkylbenzenes and benzonitriles. See also British Patent 951,770.

The compounds of this invention are excellent herbicides and are especially useful as selective herbicides for controlling weeds in the presence of desirable crops, especially the control of grassy weeds, such as water grass and crabgrass, as well as pigweed.

The compounds can be applied as both a pre-emergence or a post-emergence treatment; that is they can be applied to soil in which the weeds will grow or they can be used to kill or suppress the growth of growing weeds or to kill or prevent the emergence of seedlings of undesirable plants. Thus, the compounds can be used to control the growth of weeds by applying a phytotoxic amount of one or more of the active compounds of this invention to the locus to be protected, that is, soil in which the weeds are growing or will grow or the foliage of the growing plants. "Weeds" as used herein is meant to include any plant growth which is undesirable.

Generally an application rate of from about 0.5 to about 25 pounds of one or more of the active compounds per acre is effective in controlling plant growth. Preferably an application rate of from about 1 to about 8 pounds per acre is employed. At such rates, undesirable weeds are killed or stunted with little or no injury to desirable crops.

The following examples illustrate the herbicidal activity of typical compounds of this invention.

EXAMPLE IX

The compounds to be tested were evaluated as both a pre-emergence and post-emergence treatment. Greenhouse flats were planted to soybeans (SB), velvet leaf (VL), oats (O) and millet (M) and the flats sprayed on the same day as planting with an ethanol-dioxane solution of the compound to be tested at a rate of 5 pounds per acre.

Another set of flats with the same plants was treated after the plants had emerged and were about one inch in height. These flats were also sprayed with an ethanol-dioxane solution of the compound to be tested at a rate of 5 pounds per acre. The flats were kept in the greenhouse and watered when needed. Twenty-one days after treatment the flats were examined and the plants rated for herbicidal activity on a 0 to 9 scale in which 0 = no effect, 5 = substantial injury with some kill, and 9 = complete kill. The following results were obtained.

TABLE I

| COMPOUND | ACTIVITY | | | | | | | |
|---|---|---|---|---|---|---|---|---|
| | Pre | | | | Post | | | |
| | SB | VL | O | M | SB | VL | O | M |
| $N^3,N^3$-diethyl-2,4-dinitro-6-methyl-1,3-phenylenediamine | 1 | 4 | 2 | 9 | 3 | 7 | 0 | 6 |
| $N^3,N^3$-di-n-propyl-2,4-dinitro-6-methyl-1,3-phenylenediamine | 1 | 2 | 1 | 9 | 3 | 6 | 5 | 6 |
| $N^1,N^3$-diethyl-2,4-dinitro-6-methyl-1,3-phenylenediamine | 1 | 2 | 1 | 8 | 2 | 2 | 3 | 7 |
| $N^3,N^3$-diethyl-2,4-dinitro-6-cyano-1,3-phenylenediamine | 1 | 4 | 4 | 9 | 2 | 4 | 2 | 4 |
| $N^3$-(3-pentyl)-2,4-dinitro-6-methyl-1,3-phenylenediamine | 2 | 4 | 5 | 9 | 3 | 4 | 1 | 5 |
| $N^1,N^3$-diisopropyl-2,4-dinitro-6-methyl-1,3-phenylenediamine | 0 | 0 | 0 | 0 | 1 | 2 | 0 | 2 |
| $N^3$-sec-butyl-2,4-dinitro-6-methyl-1,3-phenylenediamine | 0 | 3 | 0 | 9 | 1 | 4 | 0 | 5 |

Since a relatively small amount of one or more of the active 2,4-dinitro-1,3-phenylenediamines should be uniformly distributed over the area to be treated, the compounds preferably are formulated with conventional herbicide carriers, either liquid or solid. Thus, the compounds can be impregnated on or admixed with a pulverulent solid carrier such as lime, talc, clays, Bentonite, calcium chloride, vermiculite, calcium carbonate, and the like. Alternatively, the compounds can be dissolved or suspended in a liquid carrier such as water, kerosene, alcohols, diesel oil, xylene, benzene, glycols, ketones, and the like. A surfactant preferably is included to aid in dispersion, emulsification and coverage. The surfactant can be ionic or non-ionic, and may be liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they may be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 99 percent by weight of one or more of the active 2,4-dinitro-1,3-phenylenediamines with a carrier or diluent, which may be a liquid or a solid. Liquid carriers which are miscible with the active agent or other liquids in which the compound may be suspended or dispersed can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Also, other herbicides such as the sodium borates, sodium chlorate, chlorophenoxyacetic acids, substituted uracils and ureas, triazines, benzimidazoles, carbamates, amides, and haloalkanoic acids, can be included in the formulation.

Various changes and modifications of the invention can be made and, to the extent that such variations incorporate the spirit of this invention, they are intended to be included within the scope of the appended claims.

What is claimed is:

1. A compound of the formula

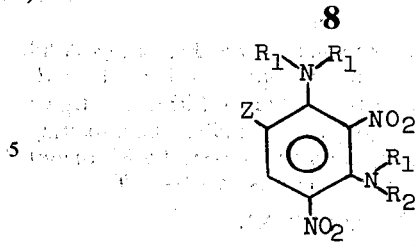

in which Z is cyano, each $R_1$ is selected from the group consisting of hydrogen, alkyl and alkenyl and $R_2$ is selected from the group consisting of alkyl and alkenyl, said alkyl and alkenyl groups having up to about six carbon atoms.

2. A compound in accordance with claim 1 in which $R_2$ is alkyl.

3. A compound in accordance with claim 1 in which $$-N\begin{matrix}R_1\\R_1\end{matrix}$$

and $$-N\begin{matrix}R_1\\R_2\end{matrix}$$

are different.

4. A compound in accordance with claim 1 in which each $R_1$ is hydrogen and $R_2$ is 3-pentyl.

5. A compound in accordance with claim 3 in which $$-N\begin{matrix}R_1\\R_1\end{matrix}$$

is $-NH_2$.

6. The compound in accordance with claim 1, $N^3,N^3$-diethyl-2,4-dinitro-6-cyano-1,3-phenylenediamine.